(12) United States Patent
Xu et al.

(10) Patent No.: US 11,904,126 B2
(45) Date of Patent: Feb. 20, 2024

(54) CRYO FORMULATION-BASED MICRONEEDLE DEVICE FOR TRANSDERMAL DELIVERY OF BIOACTIVE THERAPEUTIC AGENTS AND PERFORMING VACCINATION USING A CRYO-MICRONEEDLE PATCH

(71) Applicant: City University of Hong Kong, Kowloon (HK)

(72) Inventors: Chenjie Xu, Kowloon (HK); Hao Chang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 265 days.

(21) Appl. No.: 17/443,513

(22) Filed: Jul. 27, 2021

(65) Prior Publication Data

US 2023/0033564 A1 Feb. 2, 2023
US 2023/0285730 A9 Sep. 14, 2023

Related U.S. Application Data

(60) Provisional application No. 63/071,491, filed on Aug. 28, 2020.

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01);
(Continued)

(58) Field of Classification Search
CPC ...... A61M 37/0015; A61M 2037/0023; A61M 2037/0053; A61M 2037/0061;
(Continued)

(56) References Cited

U.S. PATENT DOCUMENTS

| | | | |
|---|---|---|---|
| 2002/0091357 A1* | 7/2002 | Trautman | A61B 17/205 606/186 |
| 2005/0123565 A1* | 6/2005 | Subramony | A61N 1/30 424/234.1 |

(Continued)

FOREIGN PATENT DOCUMENTS

WO 2015/132568 9/2015

*Primary Examiner* — Amber R Stiles
(74) *Attorney, Agent, or Firm* — Renner, Kenner, Greive, Bobak, Taylor & Weber

(57) ABSTRACT

A cryo formulation-based microneedle device for transdermal delivery of bioactive therapeutic agents. The microneedle device includes: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on a skin surface, in which the miniaturized needles penetrates into skin; wherein the miniaturized needles is further arranged to melt so as to release one or more bioactive therapeutic agents into the skin to achieve a targeted therapeutic effect; and wherein the bioactive therapeutic agents includes protein and/or antigens.

20 Claims, 16 Drawing Sheets
(2 of 16 Drawing Sheet(s) Filed in Color)

(52) U.S. Cl.
CPC ............ *A61M 2037/0061* (2013.01); *A61M 2202/0007* (2013.01); *A61M 2202/03* (2013.01); *A61M 2202/07* (2013.01); *A61M 2202/30* (2013.01)

(58) Field of Classification Search
CPC ...... A61M 2202/0007; A61M 2202/03; A61M 2202/07; A61M 2202/30; A61M 2037/0046; A61K 47/26; A61K 47/36; A61K 9/0021
See application file for complete search history.

(56) References Cited

U.S. PATENT DOCUMENTS

| | | | |
|---|---|---|---|
| 2010/0114348 A1* | 5/2010 | Boyden | ................. G16H 50/50 700/109 |
| 2017/0050010 A1* | 2/2017 | McAllister | ............ B33Y 80/00 |
| 2019/0046479 A1 | 2/2019 | Pathak | |
| 2022/0062606 A1* | 3/2022 | Chen | ..................... B29C 39/026 |
| 2023/0038697 A1* | 2/2023 | Xu | .................... A61M 37/0015 |

* cited by examiner

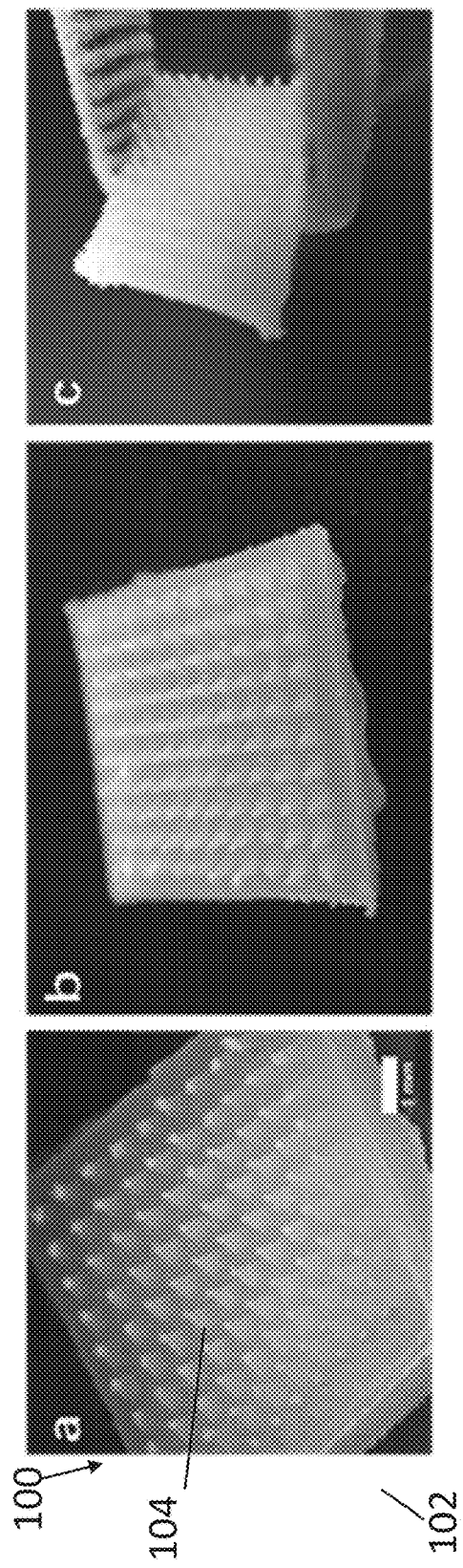
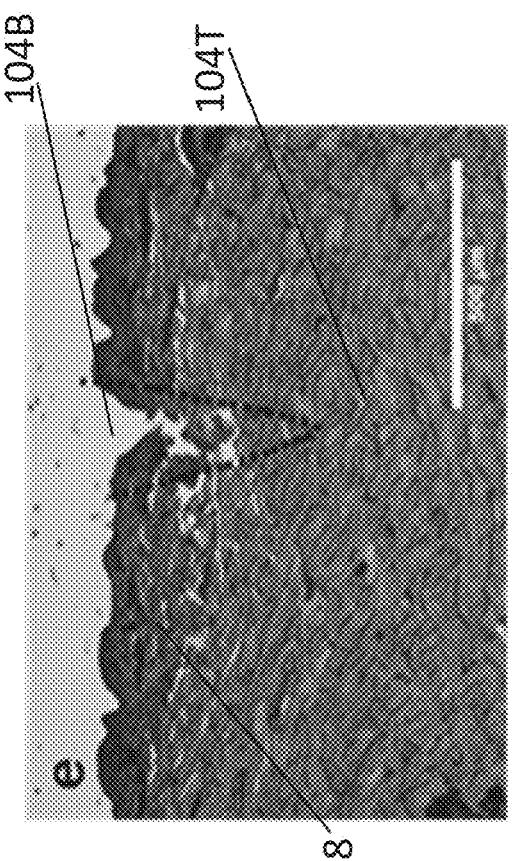
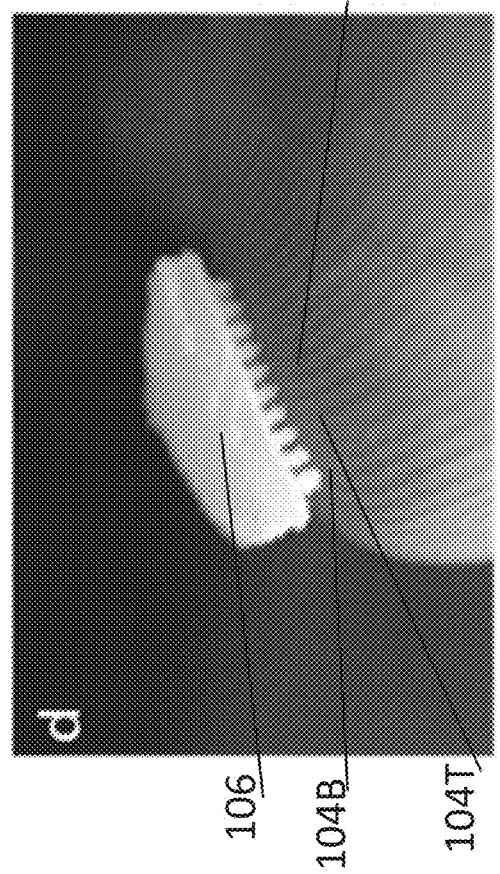
FIG. 1A
FIG. 1B
FIG. 1C
FIG. 1D
FIG. 1E

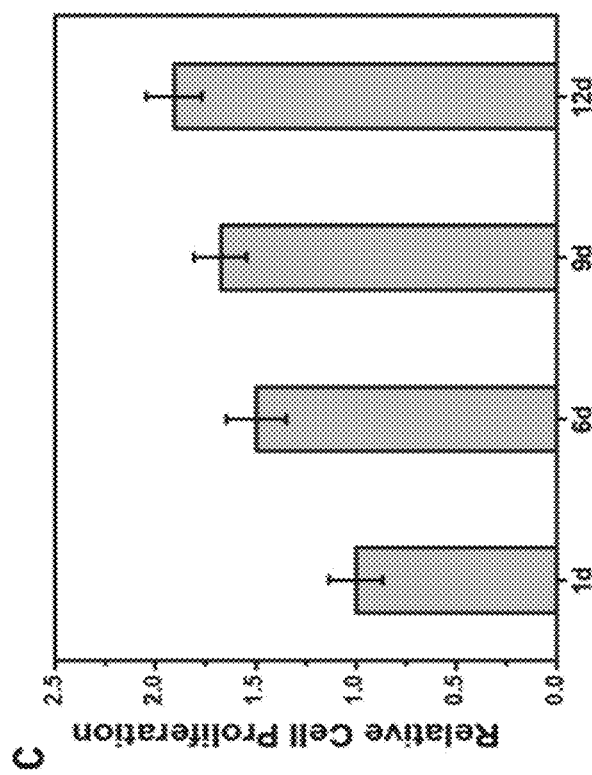
FIG. 6C
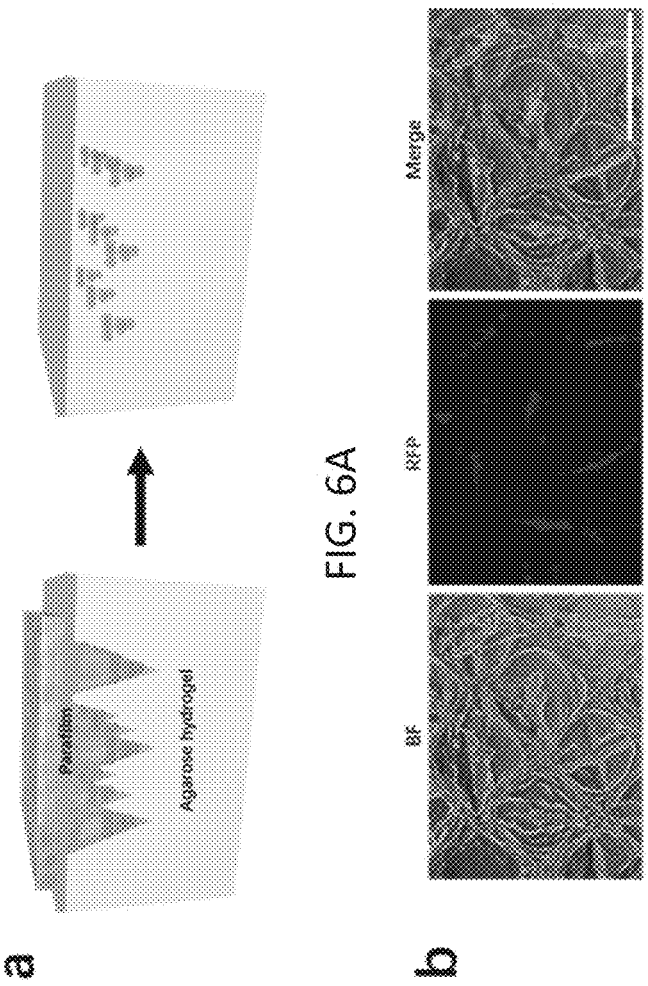
FIG. 6A
FIG. 6B

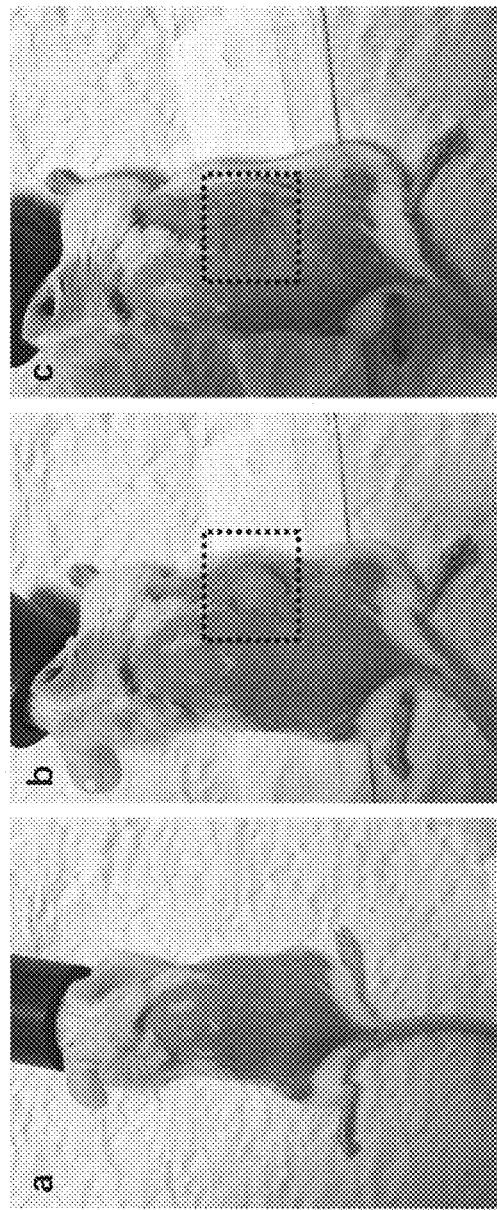
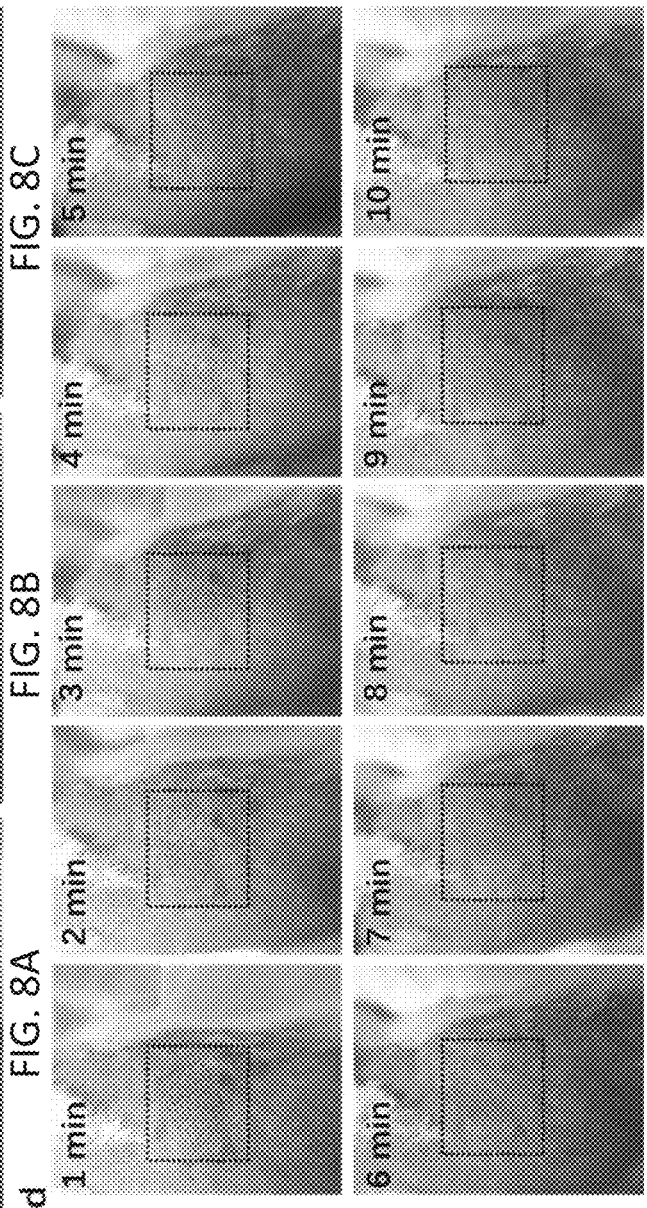
FIG. 8A  FIG. 8B  FIG. 8C  FIG. 8D

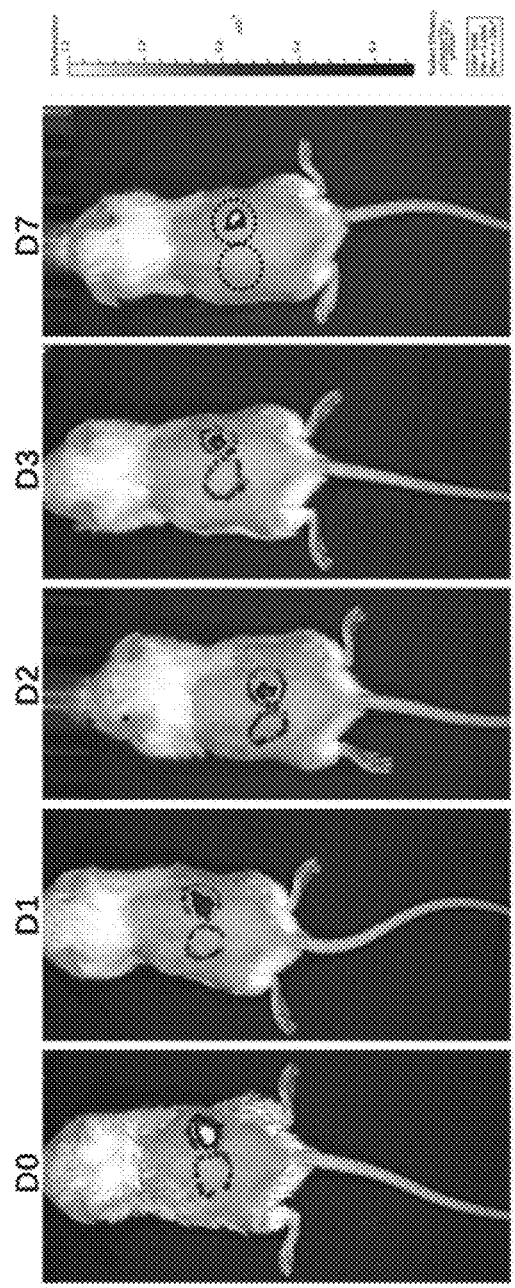
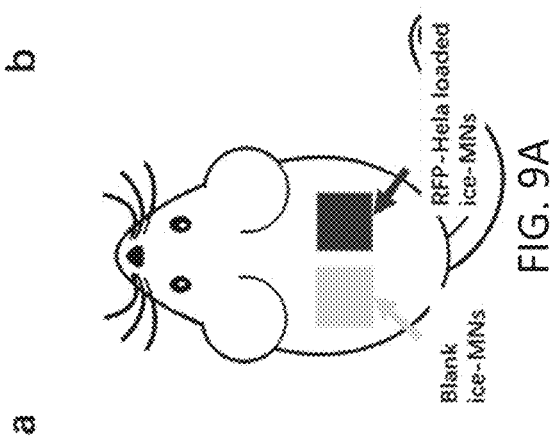
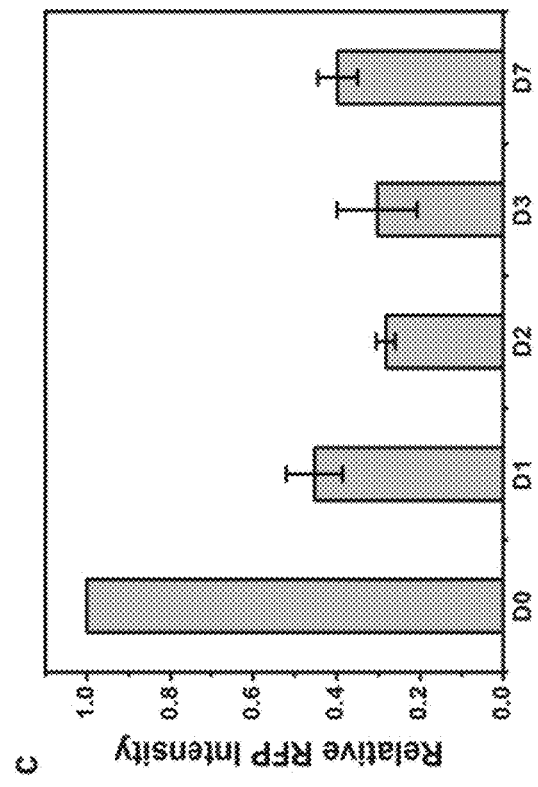
FIG. 9A
FIG. 9B
FIG. 9C

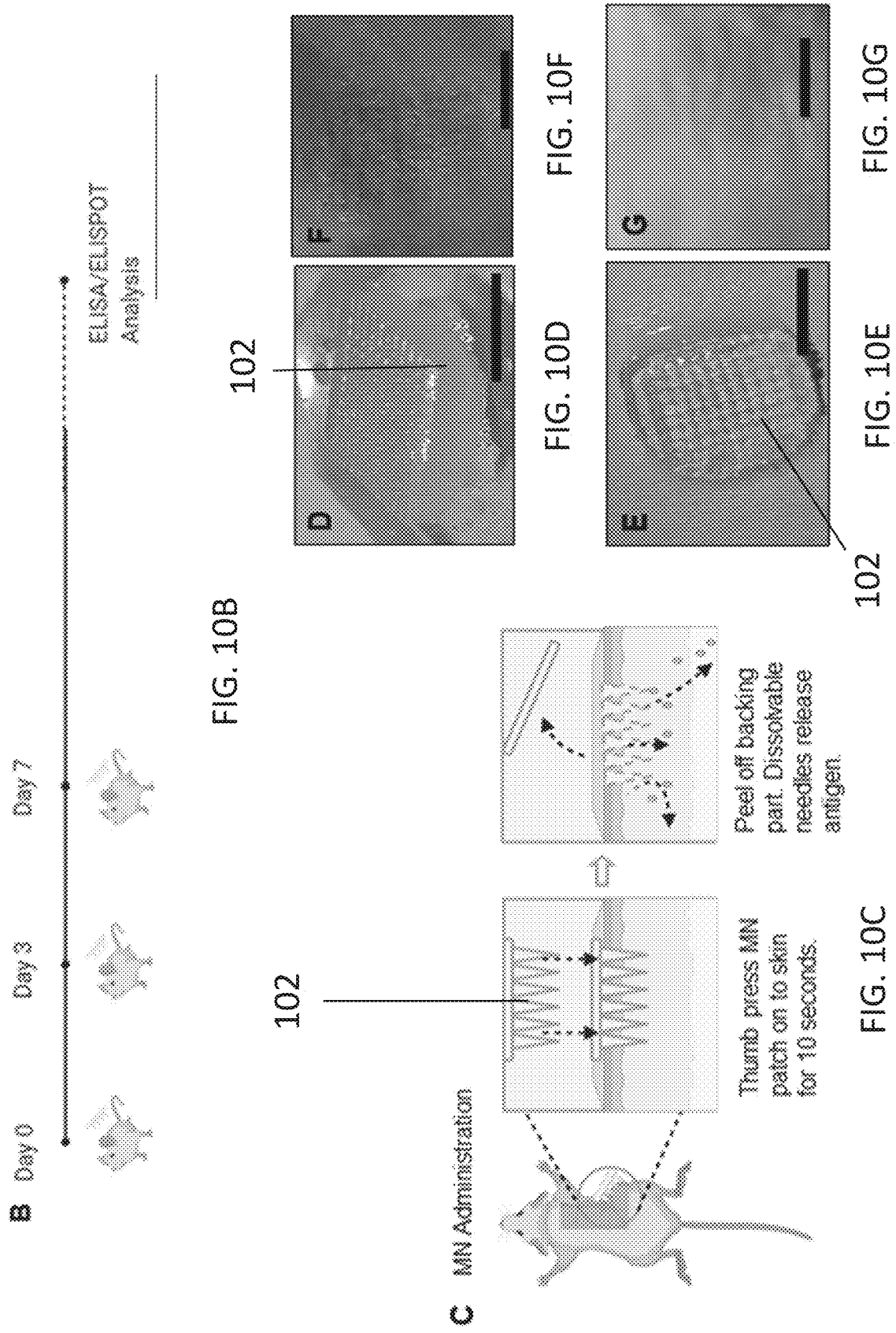

CRYO FORMULATION-BASED MICRONEEDLE DEVICE FOR TRANSDERMAL DELIVERY OF BIOACTIVE THERAPEUTIC AGENTS AND PERFORMING VACCINATION USING A CRYO-MICRONEEDLE PATCH

TECHNICAL FIELD

The present invention relates to a cryo formulation-based microneedle device for transdermal delivery of bioactive therapeutic agents, in particular, but not limited to transdermal delivery of vaccines such as mRNA antigens.

BACKGROUND

Delivery of bioactive agents is of great potential for treatment skin diseases. For example, melanocyte suspensions have been used clinically to vitiligo. Intradermal injection of fibroblast or mesenchymal stem cell was used for wound healing in recessive dystrophic epidermolysis bullosa.

In addition to treat skin diseases, transplantation of cells is also used in the field of facelift and hair regeneration. For example, injection of fibroblast can help restore the elasticity of skin and reduce winkles because fibroblasts can produce a large amount of collagen which can recover skin.

SUMMARY OF THE INVENTION

In accordance with a first aspect the present invention, there is provided a cryo formulation-based microneedle device for transdermal delivery of bioactive therapeutic agents, comprising: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on a skin surface, in which the miniaturized needles penetrates into skin; wherein the miniaturized needles is further arranged to melt so as to release one or more bioactive therapeutic agents into the skin to achieve a targeted therapeutic effect; and wherein the bioactive therapeutic agents includes protein and/or antigens.

In an embodiment the first aspect, each of the one or more microneedle patches consisting of a matrix solution and the bioactive therapeutic agents.

In an embodiment the first aspect, the matrix solution consists of an aqueous base solution and a cryoprotectant.

In an embodiment the first aspect, the aqueous base solution comprises at least one of water, phosphate-buffered saline (PBS), and 4-(2-hydroxyethyl)-1-piperazineethanesulfonic acid (HEPES).

In an embodiment the first aspect, the cryoprotectant include at least one of dimethyl sulfoxide (DMSO), glycerol, ethylene glycol, sucrose, fructose, trehalose, galactose, dextrose and proteins.

In an embodiment the first aspect, the cryoprotectant include at least one of poly(ethylene glycol) (PEG), polyvinylpyrrolidone (PVP), polyvinyl alcohol (PVA), poly-l-lysine, hyaluronic acid (HA), starch, gelatin, agarose, alginate, chitosan, cellulose, carboxymethyl cellulose (CMC), collagen, chitin, dextran, guar gum, pullulan, xanthan, xyloglucan, heparin, chondroitin, keratan, mucin, and their derivatives thereof.

In an embodiment the first aspect, the matrix solution further comprises hyaluronic acid and/or a buffered solution.

In an embodiment the first aspect, wherein the buffered solution includes phosphate buffered saline (PBS).

In an embodiment the first aspect, the antigens includes mRNA antigens.

In an embodiment the first aspect, the antigens includes spike glycoprotein (S protein) and/or nucleocapsid protein (NP).

In an embodiment the first aspect, the bioactive therapeutic agents further comprises an mRNA carriers.

In an embodiment the first aspect, the mRNA carriers include polyethylenimine (PEI) and/or protamine.

In accordance with a second aspect the present invention, there is provided a method of fabricating a microneedle device in the first aspect, comprising the steps of: casting the matrix solution containing the bioactive therapeutic agents into a mold defined with an array of microneedle structures; freezing the solution to define the array of microneedle structures on the microneedle patches; and dethatching the microneedle patches from the mold; and storing the microneedle patches below −80° C.

In an embodiment the second aspect, the mold includes a PDMS mold or a metal mold.

In an embodiment the second aspect, the method further comprises the step of urging the bioactive therapeutic agents and/or the matrix solution into the array of microneedle structures define on the mold.

In an embodiment the second aspect, the bioactive therapeutic agents and/or the matrix solution are driven into the mold using centrifugation.

In an embodiment the third aspect, there is provided a method of using the microneedle device of the first aspect, comprising the step of: removing the microneedle device from a storage place at a temperature of below −80° C.; and applying the microneedle device within a predetermined period of time after removal from the storage place.

In an embodiment the third aspect, the predetermined period of time is 30 seconds.

In an embodiment the third aspect, the microneedle patches are arranged to facilities a predetermined penetration depth of the bioactive therapeutic agents into the skin.

In an embodiment the third aspect, the predetermined penetration depth is 50-1000 μm.

In an embodiment the third aspect, the method further comprises the step of temporally attaching the microneedle device to a handle, thereby allowing an operator to apply the microneedle device by holding the handle.

The term "comprising" (and its grammatical variations) as used herein are used in the inclusive sense of "having" or "including" and not in the sense of "consisting only of".

It should be understood that alternative embodiments or configurations may comprise any or all combinations of two or more of the parts, elements or features illustrated, described or referred to in this specification.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, in any other country.

As used herein, the term "and/or" includes any and all possible combinations or one or more of the associated listed items, as well as the lack of combinations when interpreted in the alternative ("or").

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Details and embodiments of the indoor navigation method and system will now be described, by way of example, with reference to the accompanying drawings in which:

FIGS. 1A to 1D are images showing different view of the ice microneedles integrated with living cells in accordance with embodiments of the present invention;

FIG. 1E is an image showing an H&E-stained cross-section of porcine skin after being penetrated by ice microneedles of FIG. 1A;

FIGS. 4A and 4B illustrate the viability of different types of cells after recovering from ice-MNs (freezer at −80° C.) patches and ice-MNs (LN) after 1 day storage, in which FIG. 4A shows live (green)/dead (red) staining of loaded cells, with the scale bar of 200 μm, and FIG. 4B is a plot showing quantitative data of viability obtained from the Live/Dead staining and Alarmablue™ viability assay;

FIGS. 6A to 6D illustrates a delivery of RFP-Hela cells into 3D hydrogel system, the RFP-Hela loaded ice-MNs were storage in LN for 1 day, and in which: FIG. 6A is a schematic illustration of ice-MNs(LN) penetrating into fake skin model made from 1.4% agarose gel and parafilm; FIG. 6B are microscopic images showing a top view of the hydrogel after application of ice-MN patches; FIG. 6C is a plot showing the proliferation of RFP-Hela cells after being delivered into hydrogel; and FIG. 6D is a z-stack showing the 3D hydrogel system in 1, 6, 9 and 12 days respectively;

FIGS. 8A to 8D are images showing an application of ice-MNs on mice, the RFP-Hela loaded ice-MNs were storage in LN for 1 day, in which FIGS. 7A to 7C respectively shows before (a), during (b) and after (c) application of ice-MNs (LN) on mice skin, wherein FIG. 7D shows a series of images showing the skin recovery post the treatment, and the microholes made by MN patch gradually disappeared within 10 min;

FIG. 9A is a Schematic diagram showing an application of RFP-Hela loaded ice-MNs (LN) in the mice model;

FIG. 9B are in vivo fluorescence images of RFP secreted by RFP-Hela after being delivered into skin;

FIG. 9C is a plot showing the quantitative data of RFP intensity in mice skin along with the time;

FIGS. 10B and 10C are illustrations showing a vaccination process performed on a mice and the HA-PBS cryoMN administration on the mice using the ice microneedles fabricated using the process of FIG. 10A;

FIG. 10D to 10E are images showing the ice microneedles, in which FIG. 10D was captured before deployment (tips present) (scale bar, 5 mm) and FIG. 10E was captured after deployment (tips absent) (scale bar, 5 mm)

FIG. 10F to 10G are images showing mouse skin immediately after injection (scale bar, 5 mm) and 24 hours after injection (scale bar, 5 mm) respectively;

DETAILED DESCRIPTION OF THE PREFERRED EMBODIMENT

Figure 2:
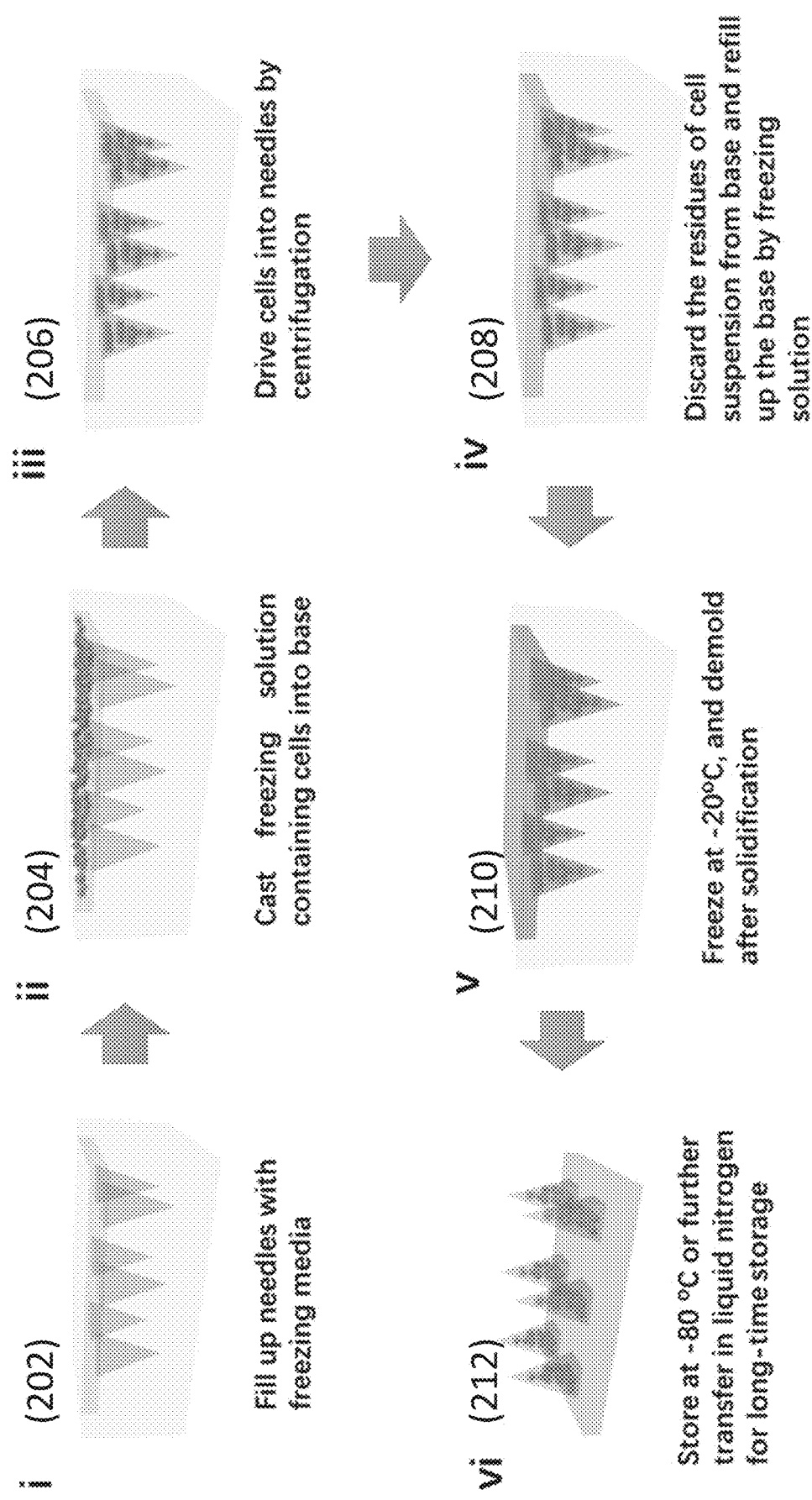
FIG. 2 is an illustration showing a process flow of a fabrication of ice microneedles integrated with living cells in accordance with an embodiment of the present invention.
Figure 3A:
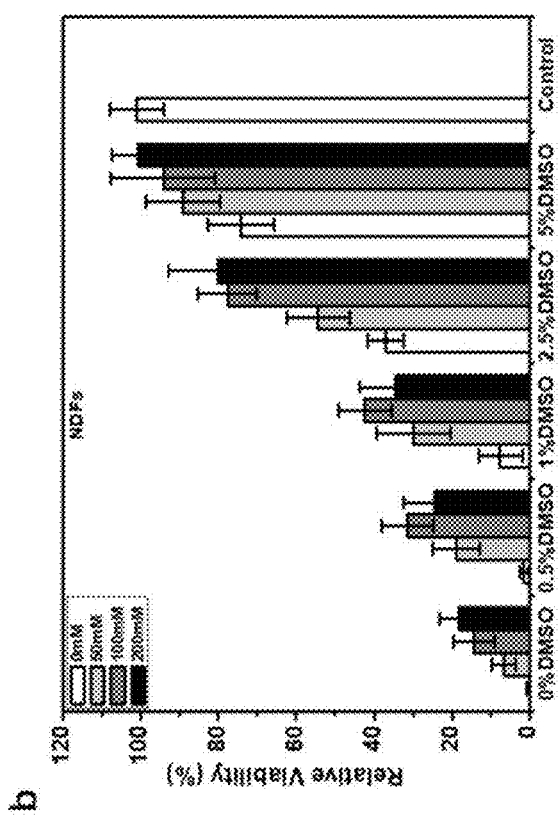
FIGS. 3A to 3F are plots showing relative viability of, RFP-Hela (a), NDFs (b), HACAT (c), MSCs (d), melanocytes (e) and T-cells (f), respectively, after being frozen in the solution with different concentrations of DMSO and sucrose at −80° C. for 1 day.
Figure 3B:
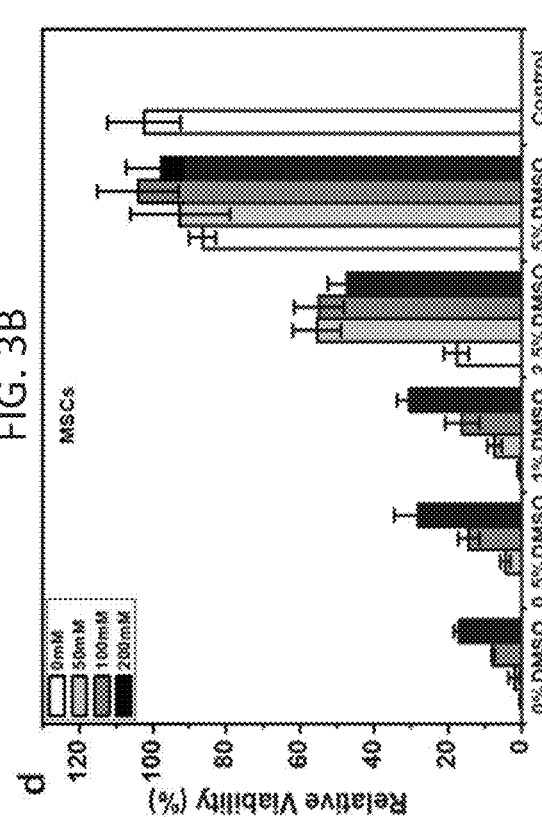
Figure 3C:
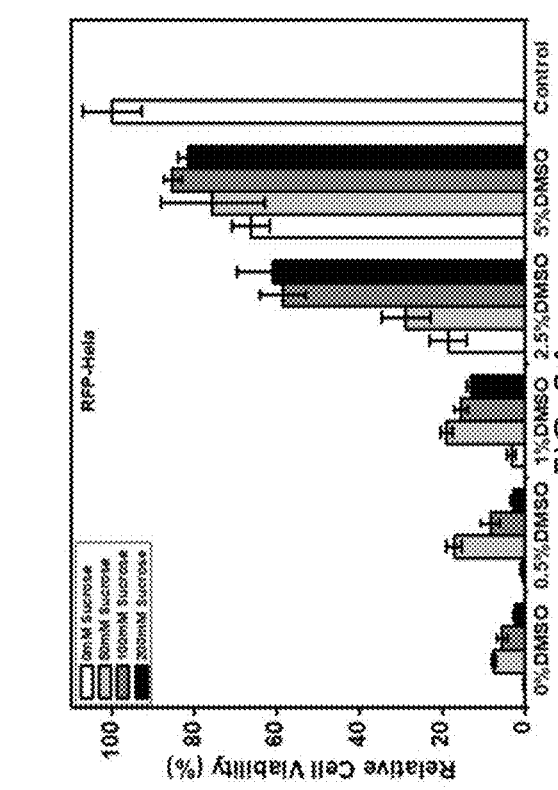
Figure 3D:
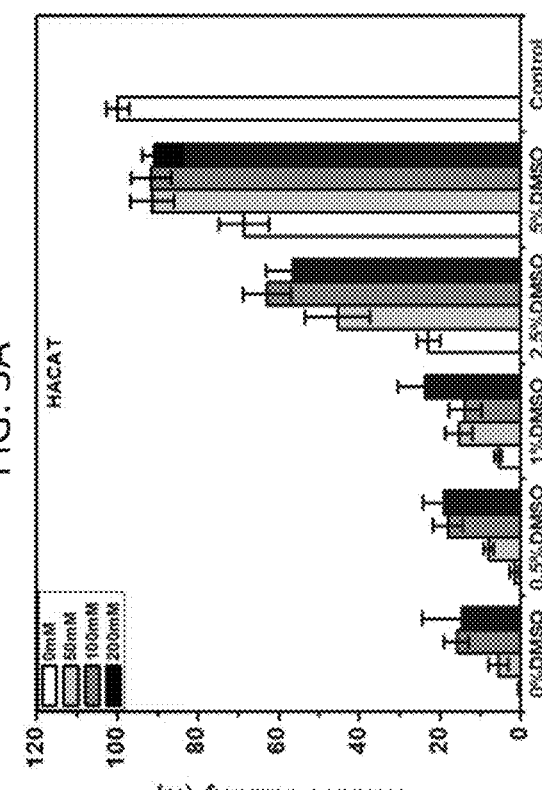
Figure 3F:
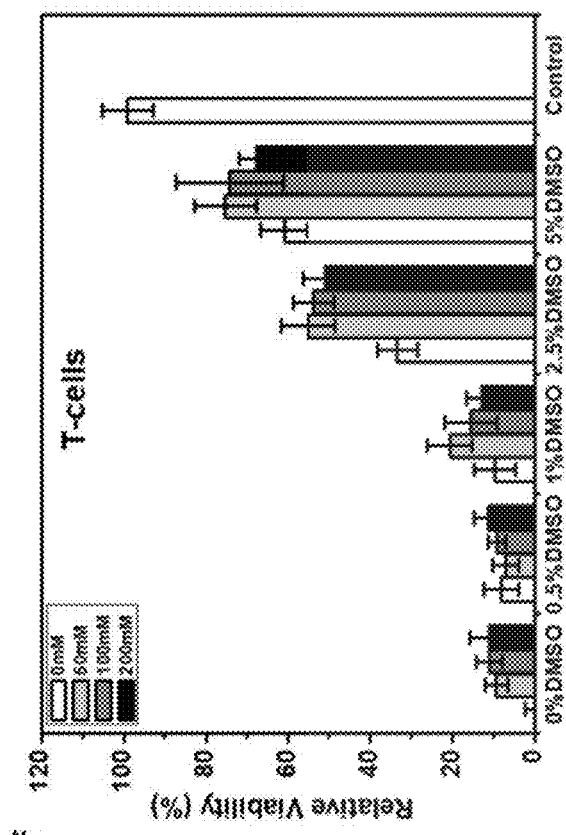
Figure 3E:
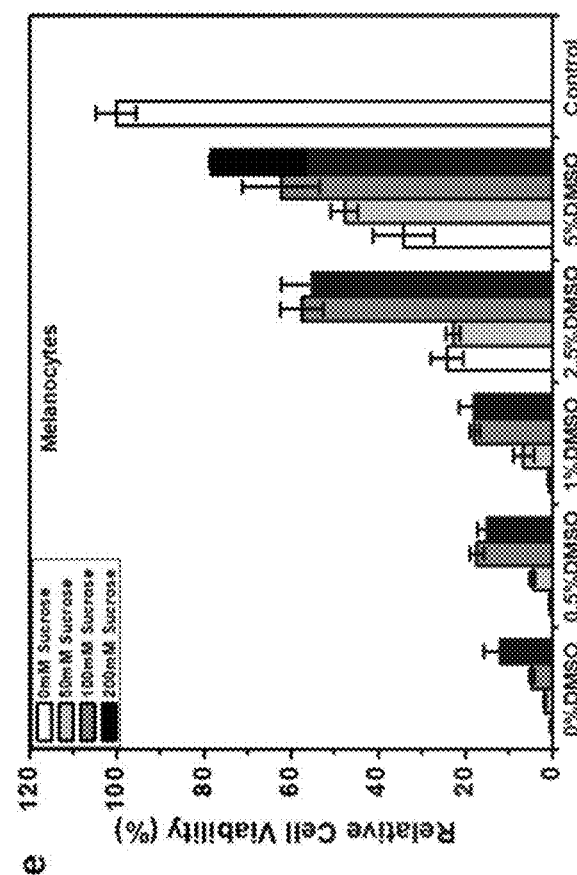

The inventors, through their own research, trials and experiments, devised that microneedles (MNs) are an array of miniaturized needles down to the micrometer scale and they are initially developed for transdermal delivery of drugs and vaccines. They allow for the minimally-invasive perturbation of the stratum corneum barrier and controlled and targeted delivery of therapeutic agents in pain-free and blood-free fashion. Recently, they are also used for the extraction of blood and interstitial fluid for biomarker analysis. MN-based devices have low risk of infection, needle-phobic and needle-stick injury and cross-contamination.

In some example embodiments, MNs may be made of silicon, metals (e.g. stainless-steel and titanium), ceramics, and polymers. However, silicon, metal and ceramics based MNs suffer from the limited drug loading, potential break-up in skin, or complicated and expensive fabrication procedures, and polymer MNs are limited by the low drug loading and inability to maintain the activity and deliver fragile active agents such as protein, plasmid, stem cells, immune cells, bacteria, and virus.

In accordance with an embodiment of the present invention, there is provided a new class of MN device, the cryo formulation-based MN device (cryo MNs, or ice MNs), which is significantly different from the abovementioned MN platforms in terms of materials, formulations, and fabrication protocols.

Preferably, this device is made of aqueous solutions and bioactive therapeutic agents (eg. cells, drugs, and proteins, et al.) and fabricated by freezing to form the cryo status. The formulation is optimized to maximize the bioactivity of therapeutic agents while providing sufficient mechanical properties for the ice MNs to penetrate into the skin layers. Finally, the ice MNs are usually made right before usage within the template (can be less than 4 hours), but can be stored for at least 1 month without loss of bioactivity or viability.

In one example embodiment, the invention provides a direct integration of cells and delivery of cells with ice MNs. The inventors devise that all other MN platforms except hollow MNs are not suitable for cell delivery, and although hollow MNs may be used to deliver cells through pressure-based injection, such system lacks of control of the injection depth, cell number, and pattern of cells.

Preferably, the ice MNs is the first type of solid MN that can deliver cells and directly integrate cells into MNs. It offers a convenient strategy to control the location, density and types of delivered cells in skin.

With reference to FIGS. 1A to 1E, there is shown an example embodiment of a cryo formulation-based microneedle device 100 for transdermal delivery of bioactive therapeutic agents, comprising: one or more microneedle patches 102 each including an array of miniaturized needles 104, wherein each miniaturized needle 104 defining a base end and a tip 104T; and a substrate 106 to which the base end of the array of miniaturized needles 104 is attached or integrated thereto; wherein the microneedle patch 102 is in a cryo status; wherein each of the one or more microneedle patch 102 is adapted to be applied on a skin surface 108, in which the miniaturized needles 104 penetrates into skin; and wherein the miniaturized needles 104 is further arranged to melt so as to release one or more bioactive therapeutic agents into the skin to achieve a targeted therapeutic effect.

In this example, the microneedle patches 102 consisting of a matrix solution containing a bioactive therapeutic agents being freezed in the solid state, such that when the ice microneedle patches 102 is subjected to heat at the skin surface 108 and/or from the environment, it melts gradually and hence the bioactive therapeutic agents is released into the skin as the patch 102 melts.

Examples of bioactive therapeutic agents may includes biological cells, such as but not limited to cancer cells, fibroblasts, endothelial cells, smooth muscle cells, stem cells, melanocytes, dendritic cells, neutrophils, and T-cells. Alternatively or additionally, the bioactive therapeutic agents may include other biochemical substances such as but not limited to drugs, vaccines, proteins, peptides, nucleic acids, bacteria, virus and fungi.

The bioactive therapeutic agents may be contained in a matrix solution, comprising an aqueous base solution and a cryoprotectant, such that the matrix solution and the bioactive therapeutic agents may be molded to have the shape of the microneedles 104 with the base. Examples of the aqueous base solution includes one or more of water, phosphate-buffered saline (PBS), and 4-(2-hydroxyethyl)-1-piperazineethanesulfonic acid (HEPES), and these aqueous base solution may be solidified upon freezing.

For example, the ice-MNs that were finally frozen either in −80° C. or liquid nitrogen (LN) were named as ice-MNs (−80° C.) and ice-MNs (LN), respectively. The morphology of ice MNs 104 is shown in the FIGS. 1A to 1D. In this example, the obtained ice-MNs 104 displayed a height of ~900 μm with a base width of about 350 μm and inter-needle spacing of about 350 μm. According to the dimension of ice-MN patch 102 and volume formula of rectangular pyramid, the volume of solution in each needle cavity was about $3.7 \times 10^{-2}$ μl. In addition, referring to FIG. 1E, the ice MNs can easily penetrate cross the epidermis and reach to dermis. It should be appreciated by a skilled person in the art that the dimension or design parameters of the MNs including the size, pitch, height and shape of the needles, as well as the area of the MNs array may be changed according to different application which requires delivery of bioactive therapeutic agents through the skin surface.

The formulation of solution for preparing ice MN depends on the desired active agents that will be delivered. The following table lists a number of example choice of several freezing solutions for different active agents.

| Active agents | Solutions |
| --- | --- |
| Cells | Water + cryoprotectants (such as 2.5% wt DMSO, 100 mM sucrose) |
| Protein/peptides | Water/PBS + 1 mg/mL Bovine serum albumin (BSA) |
| DNA/RNA | Water/PBS +1 mg/mL polycation (such as poly-l-lysine, chitosan, collagen) |
| Small molecular drugs | Water/PBS |

With reference to FIG. 2, there is shown an example fabrication process 200 for fabricating the microneedle device 100 in accordance with embodiments of the present invention. The method 200 of fabrication comprises the steps of: casting the matrix solution containing the bioactive therapeutic agents into a mold, such as a PDMS mold, defined with an array of microneedle structures; freezing the solution to define the array of microneedle structures on the microneedle patches; and dethatching the microneedle patches from the mold. Alternatively, a metal mold, such as a stainless steel mold, may be used. Preferably, the solution may be frozen −80° C. which may be more suitable for preparing microneedle patches containing protein such as mRNA or other antigens as the bioactive therapeutic agents to be applied after demoulding.

Optionally, the method further comprises the step of urging the bioactive therapeutic agents and/or the matrix solution into the array of microneedle structures define on the mold, such as by using centrifugation.

Take 2.5% wt DMSO combined with 100 mN sucrose as an example, to fabricate ice MNs 104 for cell delivery, at step 202, the mold defining the shape of the needles may be filled up with the freezing media, such as the matrix solution or the mixture of 2.5% wt DMSO combined with 100 mM sucrose. At step 204, cells contained in a freezing solution such as water and/or the cryoprotectants are casted to the mold at the base. At step 206, the cells are driven into the needle structures using centrifugation. At step 208, the residues of cell suspension from the base may be discarded, and then the base of the mold may be refilled to form the base of the MN device. At step 210, the matrix solution and the cells are frozen below the melting point of the matrix solution, e.g. at −20° C., followed by demolding the frozen patch after solidification. Finally, at step 212, the fabricated cryo formulation-based microneedle device may be stored under −80° C. and/or any other suitable environment, such as in liquid nitrogen, for long-time storage if necessary.

In an alternative example, to fabricate ice MNs for small molecular drug delivery, small molecular drug may be dissolved in aqueous with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

Alternatively, to fabricate ice MNs for proteins/peptides delivery, proteins/peptides and BSA (1 mg/mL) may be dissolved in aqueous solution with desired concentrations. The prepared solution is casted into PDMS mold and followed by centrifugation. Then the PDMS mold is put at −20° C. for 2 hours and then transferred to −80° C. Then Ice MNs integrated with small molecular drugs can be peeled out of PDMS mold before applications.

Yet alternatively, to fabricate ice MNs for DNA/RNA delivery, the DNA/RNA and polycations (1 mg/mL) are dissolved in aqueous solution with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

The solutions for making ice MNs consist of aqueous base solutions and cryoprotectants. The aqueous base solutions may include water, PBS, and/or HEPES. The cryoprotectants include DMSO, glycerol, ethylene glycol, sucrose, fructose, trehalose, galactose, dextrose, proteins, or any types of combination of two or more cryoprotectants. The cryoprotectants also include polyvinylpyrrolidone, polyvinyl alcohol, poly-l-lysine, HA, starch, gelatin, agarose, alginate, chitosan, cellulose, collagen, chitin, dextran, guar gum, pullulan, xanthan, xyloglucan, and their derivatives, and the combinations thereof. In addition, the cryoprotectants include the hydrogel systems made from abovementioned polymers.

To optimize the freezing solution for cell delivery, in an experiment performed by the inventors, six types of cells, including Hela-red fluorescent protein (RFP) stable human cell line (RFP-Hela), human keratinocytes (HACAT), human normal dermal fibroblasts (NDFs), human mesenchymal stem cells (MSCs), human melanocytes and human immune cells (T-cells) were frozen in the solution with different concentration of DMSO and sucrose. The results were shown in FIGS. 3A to 3F. Increasing DMSO concentration brings the decrease of mechanical property of ice MNs. In one preferable embodiment, to balance the mechanical property and cell viability, the optimal formulation of freezing solution for cell delivery is the combination of 2.5 wt % DMSO with 100 mM sucrose.

Figures 4A, 4B:
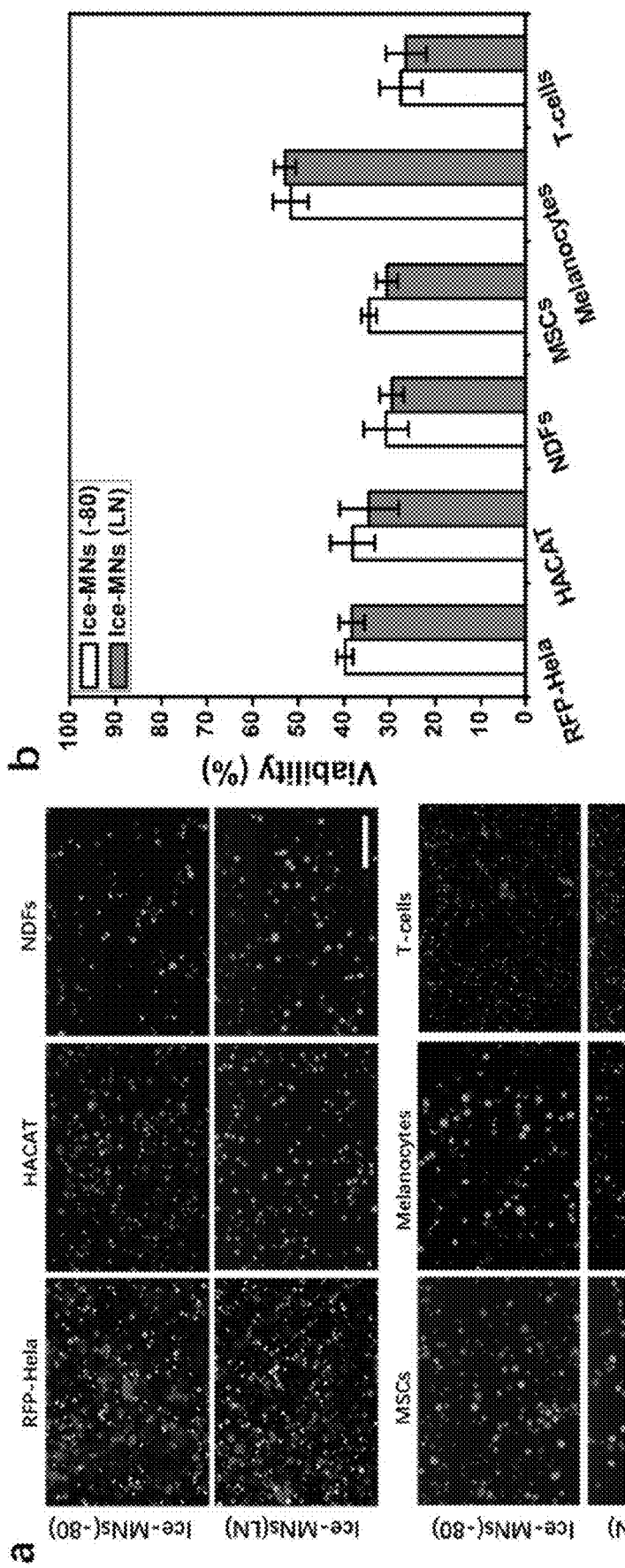
Figure 5A:
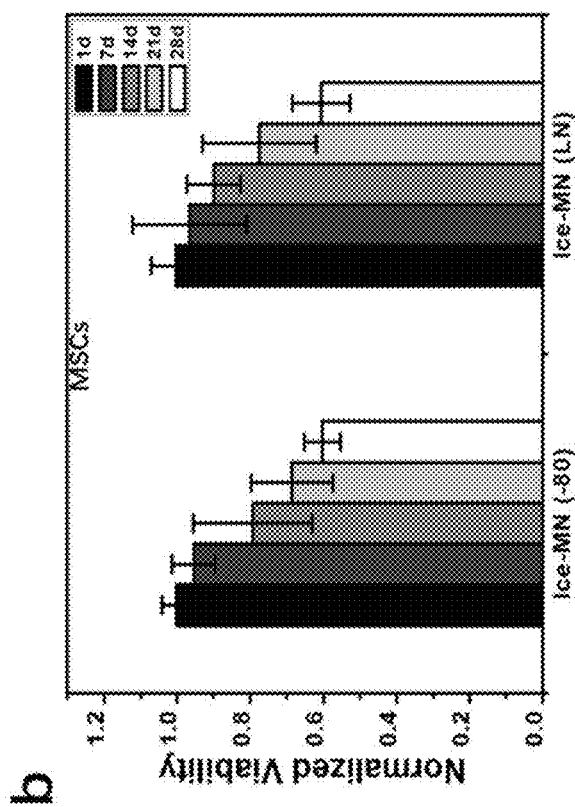
FIG. 5A to 5C are plots showing the viability of RFP-Hela (a), MSCs (b) and melanocytes (c), respectively, after recovering from ice-MNs (−80° C.) and ice-MNs (LN) for long-time storage.
Figure 5B:
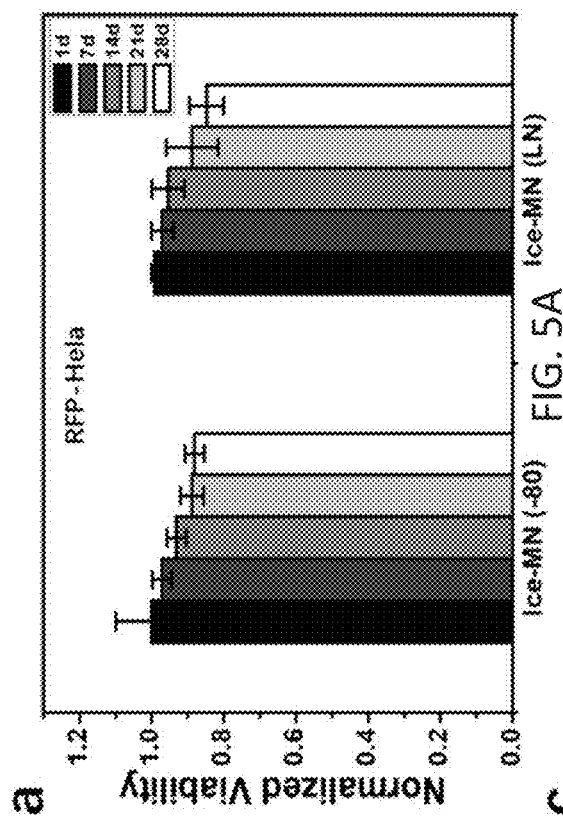
Figure 5C:
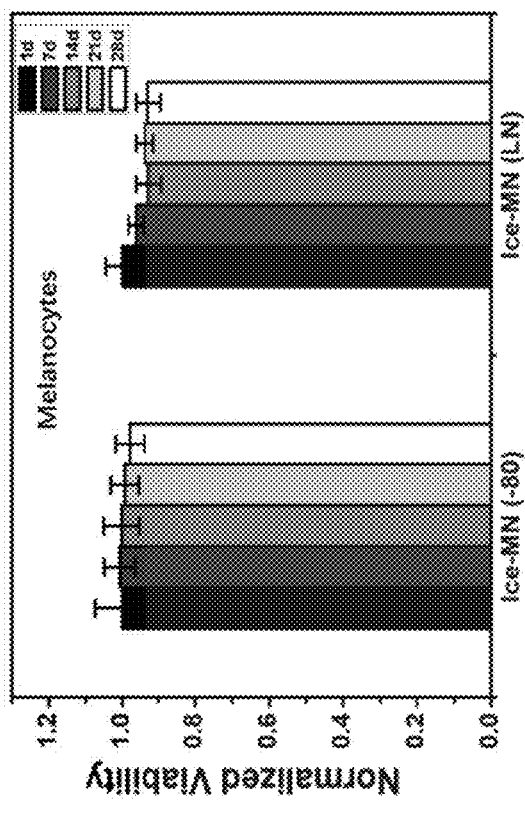

Furthermore, with reference to FIGS. 4A and 4B, the six types of cells were integrated in ice MNs and stored at freezer (−80° C.) and LN for 1 day. All types of cells maintained about 30% viability after 1-day storage. In addition, the viability of RFP-Hela, MSCs and melanocytes that were loaded in ice-MNs (−80° C.) and ice-MNs (LN) for long time storage were also tested. Referring to FIGS. 5A to 5C, it shows that cells could still maintained alive after being stored for 28 days.

Figure 6D:
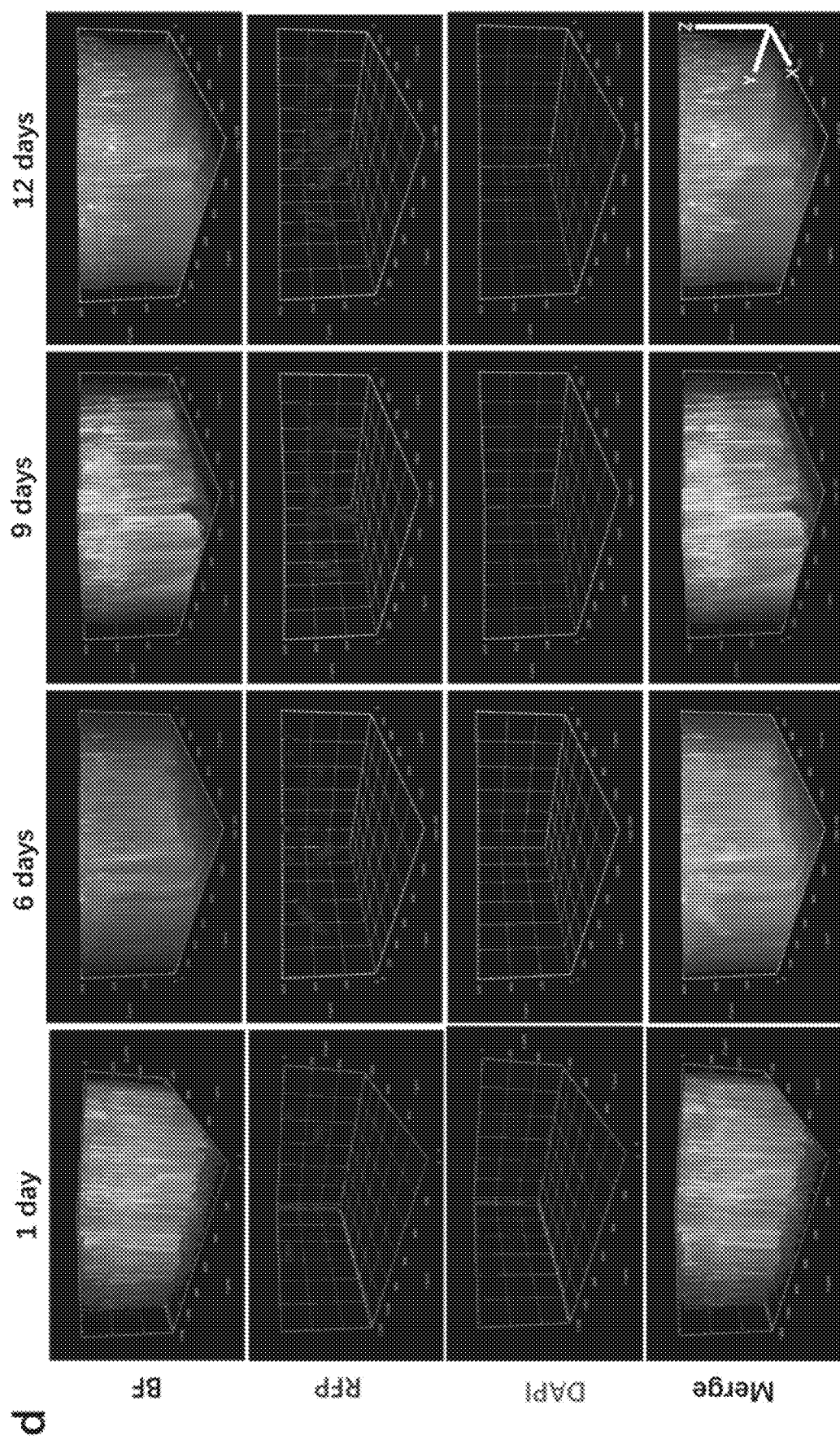

For the following experiment, the RFP-Hela loaded ice-MNs (LN) were selected as studying group and directly used after 1-day storage. The ice-MNs can successfully deliver the RFP-Hela into 3D hydrogel system (fake skin model) and the alive RFP-Hela could proliferate in this system, as shown in FIG. 6.

Figures 7A, 7B:
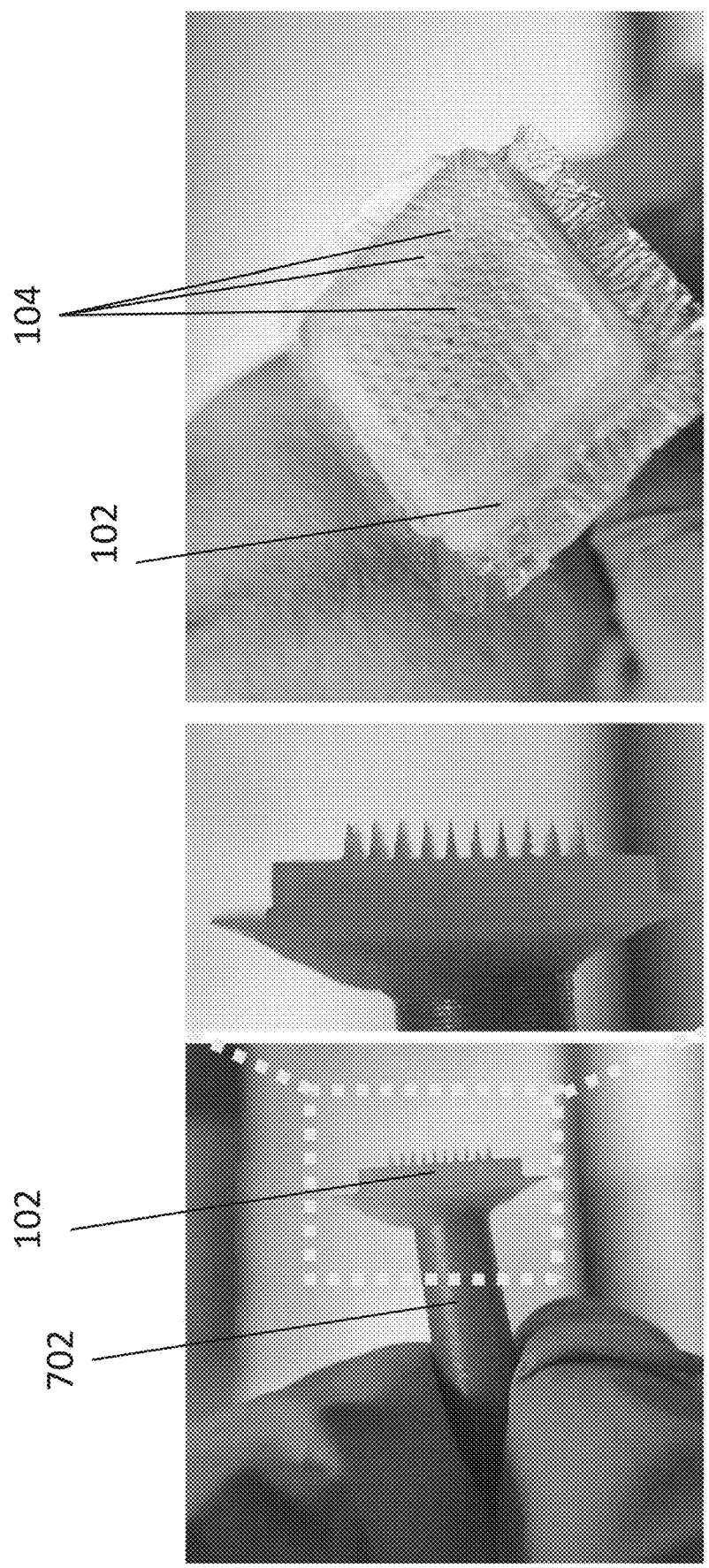
FIGS. 7A and 7B are images showing a cryo formulation-based microneedle device in accordance with an embodiment of the present invention, in which the microneedle device is attached to a handle.

With reference to FIGS. 7A and 7B, there is shown an embodiment of using the microneedle device 100 as described earlier, for example to deliver a certain dosage of RFP-Hela to mice using the MN patches 102. The method comprises the step of: removing the microneedle device 100 from a storage place; and applying the microneedle device 100 within a predetermined period of time, such as 30 seconds, after removal from the storage place.

Preferably, the microneedle patches 102 are arranged to facilities a predetermined penetration depth, such as 50-1000 μm, of the bioactive therapeutic agents into the skin.

Optionally, the method further comprises the step of temporally attaching the microneedle device 100 to a handle 702, thereby allowing an operator to apply the microneedle device 100 by holding the handle 702. For example, referring to FIGS. 7A and 7B, a rod shape handle 702 may be attached to the base of the MN patch 102 by using suitable binder, such that the operator of the patch 102 may hold the handle 702 with his thumb and index finger to apply the patch to the skin to a desired target spot, followed by removing the handle 702 from the base of the patch 102 after successfully deploying the patch 102 on the skin surface with the MNs 104 penetrating the skin surface.

In addition, an animal experiment was conducted to evaluate the performance of the apparatus fabricated in accordance with embodiments of the present invention. The RFP-Hela loaded ice MNs can easily penetrate into mice skin by the thumb force. It is clear that there was no harm effects of ice MNs on mice skin as show in FIGS. 8A to 8D, except for the microholes created by the MNs. It was also observed that the holes gradually disappeared after 10 mins as shown in FIG. 8D.

Furthermore, the ice MNs may be applied in clinic applications. The inventors monitored the intensity red fluorescent protein secreted by the delivered RFP-Hela. It demonstrated that the RFP-Hela could survive in mice skin and continued to secrete RFP after being delivered into mice skin by ice MNs as shown in FIGS. 9A to 9C. Alternatively, the ice microneedles may be used for cell delivery.

These embodiments may be advantageous in that, the ice-based MNs may be used in various treatments of skin diseases and facelift by delivering all kinds of drugs and biologics. Example applications include the treatment such as (but not limited to) vitiligo, melanoma, skin regeneration, wound healing, hair regeneration, and anti-wrinkling.

Advantageously, the MN-based device may be applied for loading and transdermal delivery of various types of bioactive therapeutic agents (e.g. therapeutic cells, small molecular drug, proteins/peptides, DNA/RNA, bacteria, virus, fungi, et al.) in a minimally-invasive manner. This device can maintain the viability and bioactivity of loaded therapeutic agents. The device has enough mechanical strength, which ensures the device can penetrate across the stratum corneum and deliver the cargo into the targeted skin layers.

By selecting and loading certain therapeutic agents, the devices can be applied for different biomedical applications, such as cancer immunotherapy (by loading dendritic cells or T cells), treatment of vitiligo (by loading melanocytes), treatment of diabetes (by loading insulin or insulin-secreting cells), treatment of topical infection (by loading probiotic bacteria or bacteriophages) and promoting skin regeneration (by loading fibroblasts or stem cells).

Embodiments of the present invention may also provide the following advantages.

Firstly, the materials of present MNs are aqueous solutions which are readily accessible and easy to prepare. For example, the 2.5% wt DMSO in water or PBS and 200 mM sucrose dissolved in water or PBS. This is different from other MN devices usually made from polymer, metal, silicon and glass, which might involve with expensive raw materials, complex chemical synthesis and potential issue of biocompatibility.

Second, the fabrication process of the device is simpler, compared with the fabrication of solid or hollow MNs.

Third, this present invention integrates living cells into MNs as a ready-to-use device and the cells can maintain alive inside the device for a long-term storage. By harnessing the device according to the embodiments of the present invention, the transdermal delivery of cells can be easily performed without assistance of any extra device. Therefore, application processes can be greatly simplified. This is particularly different from other technologies or example devices for cell delivery which may involve complex and redundant procedures including cell harvest and preparation of cell infusing solution during each administration processes, or may require additional equipment for providing infusion pressure.

Forth, the microneedle patches can also be applied for loading and delivery of many types of bioactive therapeutics, such as drugs, protein/peptides, nucleic acid, virus and bacterial, et al, for different biomedical purposes, which is different from other examples that only focus on a single type of therapeutics.

In some embodiments, the microneedle patches may specifically made for delivery of protein and mRNA antigens, for example in vaccination applications. However, the inventors devised that mRNA antigen are not suitable to be stored at room temperature, therefore the cryomicroneedle (cryoMN) encapsulating mRNA is more preferably produced and preserved at minus 80° C.

Figure 10A:
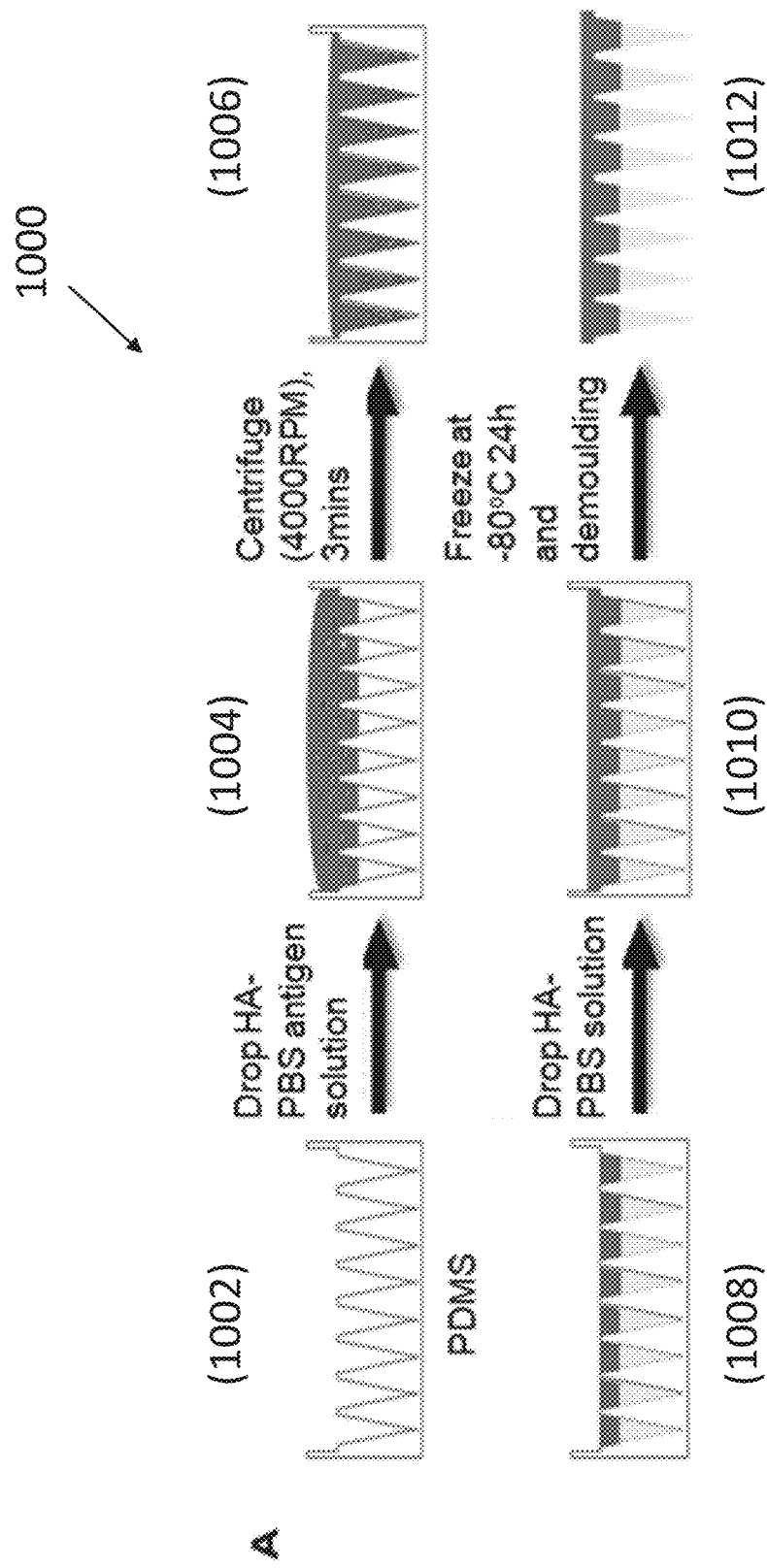
FIG. 10A is an illustration showing a process flow of a fabrication of ice microneedles integrated with protein or mRNA in accordance with an embodiment of the present invention.

Referring to FIG. 10A, there is shown an alternative process 1000 for fabricating a cryomicroneedle device. At step 1002, a PDMS mold is provided, and at step 1004, a matrix solution comprising hyaluronic acid (HA) with PBS and the target antigens may be casted into the mold. Then, at step 1006, the matrix solution and the antigens are further centrifuged to form the needle tip part. As step 1008, the mold with only the tips filled with the matrix solution and the antigens may be obtained.

At step 1010, a matrix solution without antigen (i.e. HA+PBS solution) may be added to fill the back plate to form a base of the cryomicroneedle patch. Finally, at step 1012, the mold may be frozen at minus 80° C. for 24 hours to solidify the liquid and set the cryomicroneedle patch, followed by demoulding the patch from the PDMS mould.

As appreciated by a skilled person in the art, the formula of the matrix solution, the freezing temperature and or the freezing duration may be changed if necessary, depending of the protein and/or compositions of the bioactive therapeutic agents to be encapsulated in the cryomicroneedles.

After demolding from the PDMS mould, the as fabricated cryomicroneedles device may be stored at minus 80° C. for a long period of time. To use the cryomicroneedles in vaccinations, the cryomicroneedles device may be removed from the storage place; and then may be applied to the target spot of the skin surface within a predetermined period of time after removal from the storage place, similar to the previous examples. Optionally, after pressing the MN patch 102 on the skin surface, the backing part may be removed from the skin surface such that only the tips with the antigens are left in the skin, and the needles further dissolves to release the antigens to the body of the target.

With reference to FIGS. 10B to 10G, there is shown an experimental results of a vaccination process using the HA-PBS cryoMN 102 fabricated using the process of FIG. 10A. It is observable that the microholes caused by the penetrations of MNs on the skin surface of the mouse recovers mostly after removal of the cryomicroneedle patch for 24 hours after injection.

Figure 11:
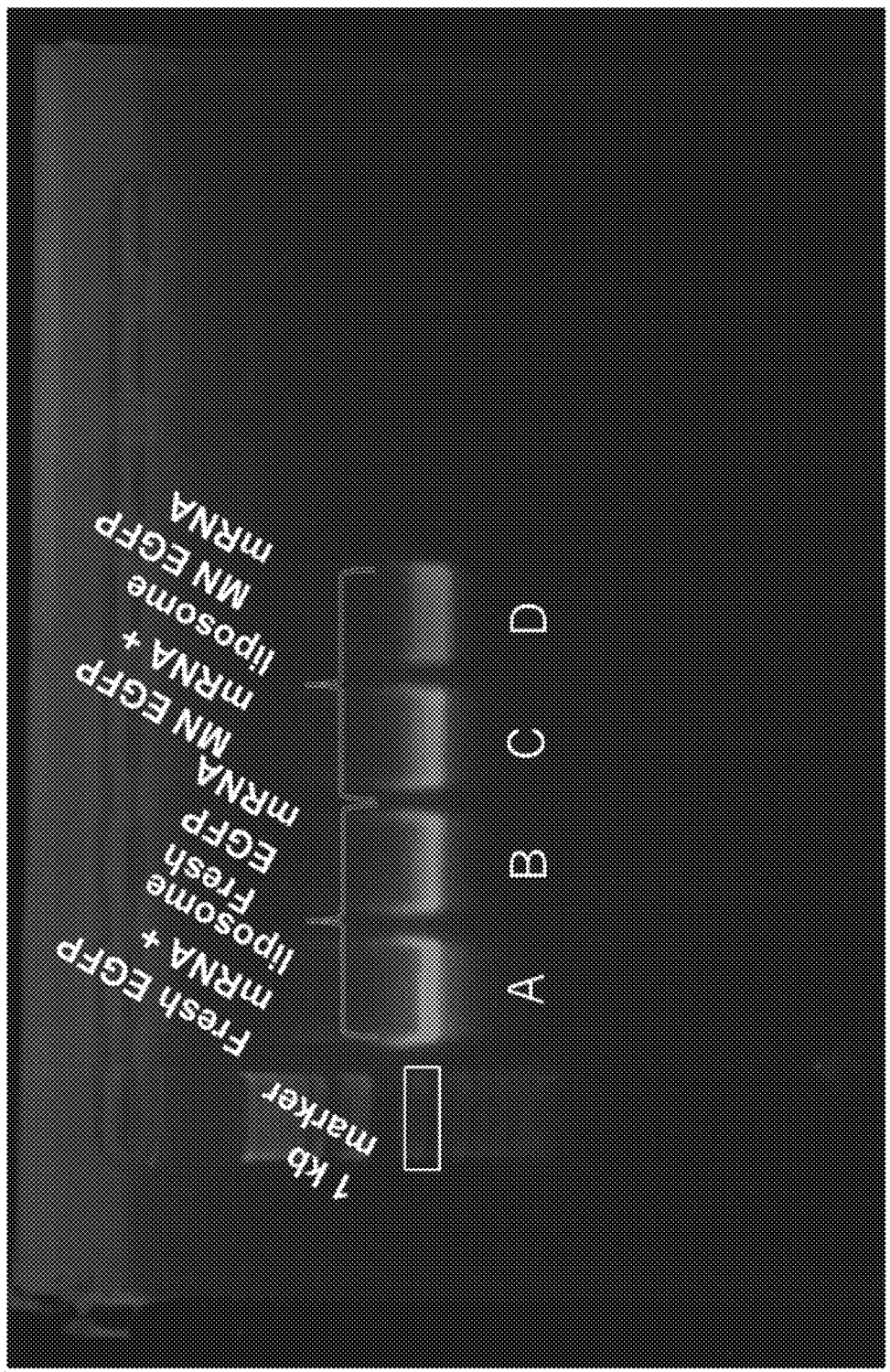
FIG. 11 is an image showing gel electrophoresis of HA-PBS cryoMN with EGFP mRNA, in which region A illustrates fresh EGFP mRNA with liposome, region B illustrates fresh EGFP mRNA, region C illustrates HA-PBS cryoMN of EGFP mRNA with liposome, and region D illustrates HA-PBS cryoMN of EGFP mRNA.

The inventors also performed experiments on gel electrophoresis after HA-PBS cryoMN dissolution using Enhanced Green Fluorescent Protein (EGFP) mRNA. With reference to FIG. 11, the results showed that the dissolved microneedles produced clear bands in the gel. The band was completely parallel to the fresh EGFP mRNA and appeared in the range of 1 kb, and addition of liposome does not affect this result. The results were consistent with the expectation and proved that EGFP mRNA was not decomposed in the microneedles.

Figures 12A, 12B, 12C:
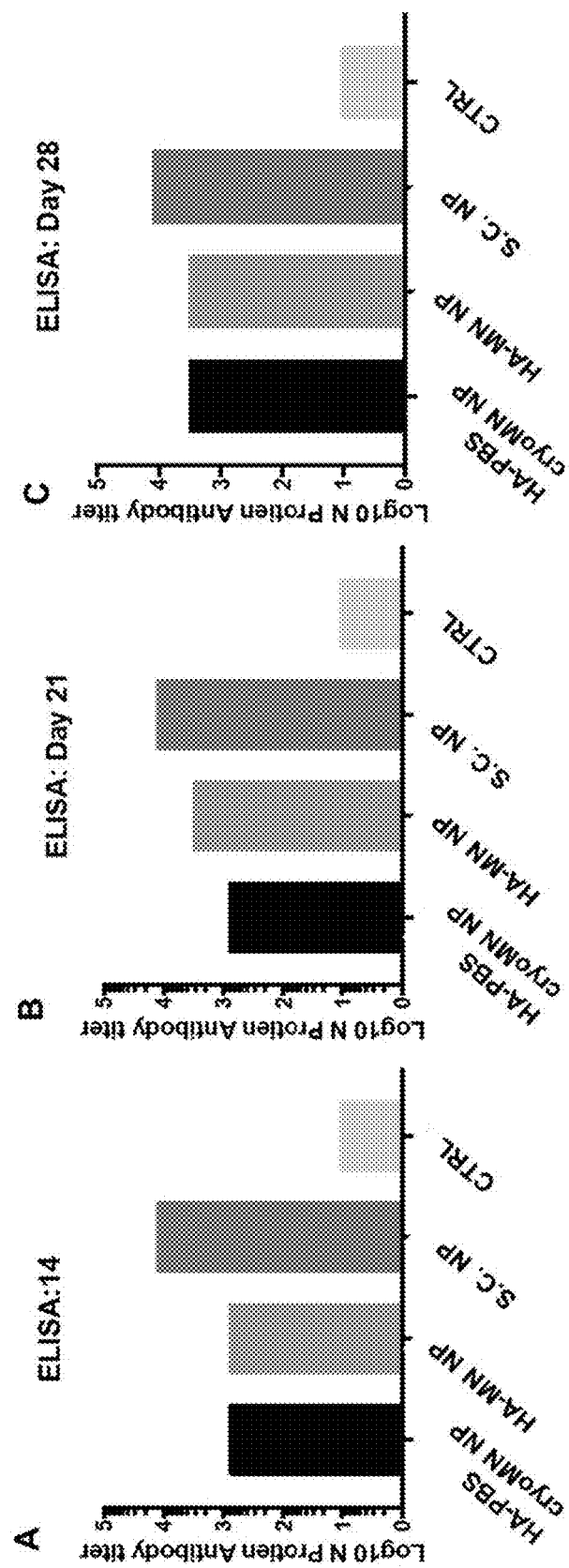
FIGS. 12A to 12C are plots showing experimental results of specific B cell antibody responses to vaccination, in which ELISA results of serum at respectively (A) day 14, (B) day 21, (C) day 28 post vaccination, showing Log 10 antibody titers against N protein in the S.C. NP immunization group, HA-MN NP immunization group, HA-PBS cryoMN NP immunization group and control group.

With reference to FIGS. 12A to 12C, there is shown HA-PBS cryoMN nucleocapsid protein immunizations lead to specific B cell antibody responses.

Without wishing to be bound by theory, apart from the conventional SARS-CoV-2 spike glycoprotein (S protein), the nucleocapsid protein (NP) may be an alternative in vaccine applications due to its ability to induce anti-viral cytotoxic T cell responses. NP plays a vital role in viral host cell entry and modulates virus particle assemble and release.

For example, there are many Human Leukocyte Antigen (HLA) binding peptides within NP, which could prime specific CD8+ and CD4+ T cell responses via major histocompatibility complex class 1 (MHC1) and major histocompatibility complex class 2 (MHC2) pathways respectively. The specific B cell antibody response post the delivery of NP was studied through the ELISA assay of IgG antibodies in sera against SARS-CoV-2.

The inventors performed further experiments to compared pure HA microneedles at room temperature and HA-PBS cryoMN. There were four groups including subcutaneously injected (S.C.) NP (25 μg/mice), HA-MN delivered NP (25 μg/mice), HA-PBS cryoMN delivered NP (25 μg/mice) and MN-delivered controls. Referring to the plots as shown in FIGS. 12A to 12C, there was no significant difference between the HA-MN NP group and the HA-PBS cryoMN group. Both groups showed strong immune response at day 28. NP antibody titers could be seen at day 14 after the first immunization, which elevated at day 21, and further increased to a maximum antibody titer of 6×103 at day 28, indicating both the HA-MN and HA-PBS cryoMN delivery of NP were highly effective. In comparison, there was no comparable immune response in the control group.

Preferably, the bioactive therapeutic agents further comprises an mRNA carriers, such as polyethylenimine (PEI) and/or protamine. Due to naked mRNA cannot readily cross the cell membrane on its own, a delivery systems to enhance its cell permeation may be required. As described earlier, liposomes may not work very well at −80° C.

Preferably, in the following experiments, polyethylenimine (PEI) and protamine were chosen as mRNA carriers. Among various polymeric carriers for gene delivery, PEI is a material which may be used as a standard control in nucleic acid transfection, and different molecular weight PEI may be added to cryoMN system to increase the efficiency of mRNA delivery. Additionally or alternatively, protamine is a natural cationic protein, which gives it an excellent ability to complex nucleic acid including mRNA and provides increased uptake of mRNA and transfection capabilities.

Advantageously, these two carriers can work as normal at −80° C. Since N protein was used at −80° C. and provided normal ELISA data, protein such protamine will not be broken by low temperature. PEI also has no reason to be broken as a polymer in low temperature. Therefore, these two carriers may be used to deliver our mRNA antigen.

Figure 13:
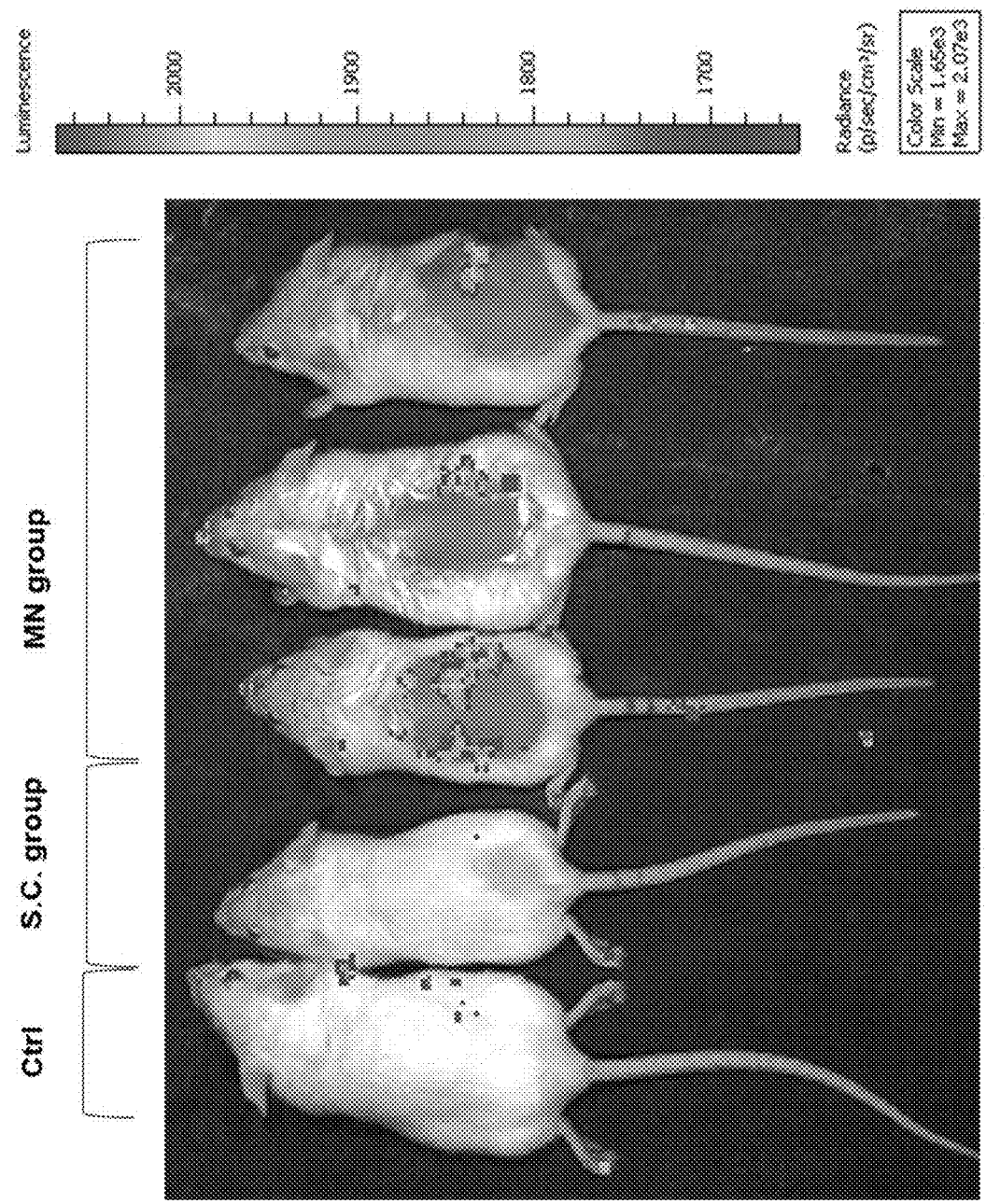
FIG. 13 is a color plot showing in vivo imaging of BALB/C mice 24 h after luciferase mRNA (S.C.), and MN-based luciferase mRNA administration compared to control. Comparison of average radiance [p/s/cm2/sr] between luciferase mRNA (S.C.) group, CryoMN PEI-based luciferase mRNA group and control group.

Preferably, luciferase mRNA may be used as a target and injected cryoMN into mouse epidermis. With reference to FIG. 13, 5 µg luciferase mRNA was mixed with 50 µl Mn 60000 50% PEI solution and 30 µl 50 mg/ml 48 k HA-PBS in the first step of microneedle preparation. After 24 h, mice were anesthetized and given a luciferin substrate (I.P.) before imaging. In the subcutaneous injection group, protamine was mixed with mRNA, but there was no signal. Pei group showed obvious fluorescence signal.

As shown in FIG. 13, average radiance [p/s/cm2/sr] between luciferase mRNA (S.C.) group, CryoMN PEI-based luciferase mRNA group and control group were compared. Significance of mean average radiance [p/s/cm2/sr] between groups was determined by unpaired parametric t-test, $p<0.0$, and the results show that the mRNA was successfully delivered to the mouse epidermis and successfully translated into protein.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A cryo formulation-based microneedle device for transdermal delivery of bioactive therapeutic agents, comprising:
    one or more microneedle patches each including an array of miniaturized needles, each miniaturized needle defining a base end and a tip; and
    a substrate to which the base end of the array of miniaturized needles is attached or integrated thereto;
    wherein the microneedle patches are in a cryo status;
    wherein each of the one or more microneedle patches are adapted to be applied on a skin surface, in which the miniaturized needles penetrate into skin;
    wherein the miniaturized needles are further arranged to melt so as to release one or more bioactive therapeutic agents into the skin to achieve a targeted therapeutic effect;
    wherein each of the one or more microneedle patches consists of a matrix solution and one or more bioactive therapeutic agents; and
    wherein the one or more bioactive therapeutic agents includes at least one of a spike glycoprotein, a nucleocapsid protein, mRNA for encoding a spike glycoprotein, mRNA for encoding a nucleocapsid protein, and a combination thereof.

2. The microneedle device according to claim 1, wherein the matrix solution comprises an aqueous base solution and a cryoprotectant.

3. The microneedle device according to claim 2, wherein the aqueous base solution comprises at least one of water, phosphate-buffered saline (PBS), and 4-(2-hydroxyethyl)-1-piperazineethanesulfonic acid (HEPES).

4. The microneedle device according to claim 2, wherein the cryoprotectant includes at least one of dimethyl sulfoxide (DMSO), glycerol, ethylene glycol, sucrose, fructose, trehalose, galactose, dextrose and proteins.

5. The microneedle device according to claim 2, wherein the cryoprotectant includes at least one of poly(ethylene glycol) (PEG), polyvinylpyrrolidone (PVP), polyvinyl alcohol (PVA), poly-l-lysine, hyaluronic acid (HA), starch, gelatin, agarose, alginate, chitosan, cellulose, carboxymethyl cellulose (CMC), collagen, chitin, dextran, guar gum, pullulan, xanthan, xyloglucan, heparin, chondroitin, keratan, mucin, and their derivatives thereof.

6. The microneedle device according to claim 1, wherein the matrix solution further comprises hyaluronic acid and/or a buffered solution.

7. The microneedle device according to claim 6, wherein the buffered solution includes phosphate buffered saline.

8. The microneedle device according to claim 1, wherein the one or more bioactive therapeutic agents further comprises mRNA carriers when the one or more bioactive therapeutic agents includes mRNA for encoding a spike glycoprotein or mRNA for encoding a nucleocapsid protein.

9. The microneedle device according to claim 8, wherein the mRNA carriers include at least one of polyethylenimine (PEI) and protamine.

10. A method of fabricating a microneedle device in accordance with claim 1, comprising the steps of:
    casting the matrix solution containing at least one of a spike glycoprotein, a nucleocapsid protein, mRNA for encoding a spike glycoprotein, mRNA for encoding a nucleocapsid protein, and a combination thereof into a mold defined with an array of microneedle structures;
    freezing the solution to define the array of microneedle structures on one of the one or more microneedle patches;
    detaching the one or more microneedle patches from the mold; and
    storing the one or more microneedle patches below −80° C.

11. The method according to claim 10, wherein the mold includes a PDMS mold or a metal mold.

12. The method according to claim 10, further comprising the step of urging the matrix solution into the array of microneedle structures defined on the mold.

13. The method according to claim 12, wherein the matrix solution is urged into the mold using centrifugation.

14. The method of claim 10, wherein the matrix solution further includes mRNA carriers when the matrix solution includes mRNA for encoding a spike glycoprotein or mRNA for encoding a nucleocapsid protein.

15. The method of claim 14, wherein the mRNA carrier includes at least one of polyethylenimine (PEI) and protamine.

16. A method of using the microneedle device in accordance with claim 1, comprising the step of:
    removing the microneedle device from a storage place at a temperature of below −80° C.; and
    applying the microneedle device within a predetermined period of time after removal from the storage place.

17. The method of claim 16, wherein the predetermined period of time is 30 seconds.

18. The method of claim 16, wherein the one or more microneedle patches are arranged to facilitate a predetermined penetration depth of the one or more bioactive therapeutic agents into the skin.

19. The method of claim 18, wherein the predetermined penetration depth is 50-1000 µm.

20. The method of claim 16, further comprising the step of temporally attaching the microneedle device to a handle, thereby allowing an operator to apply the microneedle device by holding the handle.

* * * * *